United States Patent
Paus et al.

(10) Patent No.: US 10,898,419 B2
(45) Date of Patent: Jan. 26, 2021

(54) COMPOUNDS FOR PROMOTING HAIR GROWTH AND/OR INHIBITING OR DELAYING HAIR LOSS IN HUMANS, AND COMPOSITIONS FOR SUCH USES

(71) Applicant: GIULIANI S.P.A., Milan (IT)

(72) Inventors: Ralf Paus, Hamburg (DE); Jeremy Cheret, Muenster (DE); Hanns Hatt, Bochum (DE); Sergio Baroni, Villa D'Adda (IT)

(73) Assignee: GIULIANI S.P.A., Milan (IT)

( * ) Notice: Subject to any disclaimer, the term of this patent is extended or adjusted under 35 U.S.C. 154(b) by 67 days.

(21) Appl. No.: 16/302,472

(22) PCT Filed: May 19, 2017

(86) PCT No.: PCT/EP2017/062110
§ 371 (c)(1),
(2) Date: Nov. 16, 2018

(87) PCT Pub. No.: WO2017/198818
PCT Pub. Date: Nov. 23, 2017

(65) Prior Publication Data
US 2019/0216696 A1    Jul. 18, 2019

(30) Foreign Application Priority Data

May 19, 2016    (IT) .................. 102016000051626

(51) Int. Cl.
*A61K 8/34* (2006.01)
*A61Q 7/00* (2006.01)
*A61K 31/045* (2006.01)
*A61Q 5/02* (2006.01)

(52) U.S. Cl.
CPC ............. *A61K 8/34* (2013.01); *A61K 31/045* (2013.01); *A61Q 7/00* (2013.01); *A61Q 5/02* (2013.01)

(58) Field of Classification Search
None
See application file for complete search history.

(56) References Cited

U.S. PATENT DOCUMENTS

| 4,052,341 A | 10/1977 | Naipawer et al. |
| 7,879,910 B1 | 2/2011 | Marini |
| 2017/0258739 A1 * | 9/2017 | Busse ............... A61P 17/02 |

FOREIGN PATENT DOCUMENTS

| EA | 020293 B1 | 4/2011 | |
| EP | 1238650 A2 | 9/2002 | |
| EP | 1346720 A2 | 9/2003 | |
| EP | 2916878 A1 | 9/2015 | |
| EP | 2957283 A1 | 12/2015 | |
| JP | 2006160698 A * | 6/2006 | ........ A61K 31/045 |
| WO | WO 2015193262 A1 * | 12/2015 | ........ A61K 31/045 |

OTHER PUBLICATIONS

Akada et al., CAS SciFinder (CAPLUS Acc. No. 2006:601268) English language abstract of JP 2006160698 A (Jun. 22, 2006).*
International Search Report and Written Opinion for corresponding PCT Application No. PCT/EP2017/062110 (dated Aug. 21, 2017).
Belikov, Pharmaceutical Chemistry, MEDpress-inform, pp. 27-29 (2007).

* cited by examiner

*Primary Examiner* — Brian J Davis
(74) *Attorney, Agent, or Firm* — Troutman Pepper Hamilton Sanders LLP (Rochester)

(57) ABSTRACT

The invention concerns the use of compounds of general formula (I): (I) wherein: $R_1$ and $R_2$ form together a double bond, or $R_1$ and $R_2$ form together a cyclopropyl group; $R_3$, $R_4$ are the same or different and independently chosen from hydrogen, methyl, or $R_3$ and $R_4$ form together a double bond; $R_5$, R6 are the same or different and independently chosen from hydrogen, methyl; or $R_5$ and $R_6$ form together a double bond, or $R_5$ and $R_6$ form together a cyclopropyl group; $R_7$=methyl, or ethyl; $R_8$=hydrogen, or methyl, for promoting hair growth and/or inhibiting or delaying hair loss in the human scalp, and cosmetic and pharmaceutical compositions suitable for such use.

4 Claims, 5 Drawing Sheets

COMPOUNDS FOR PROMOTING HAIR GROWTH AND/OR INHIBITING OR DELAYING HAIR LOSS IN HUMANS, AND COMPOSITIONS FOR SUCH USES

This application is a national stage application under 35 U.S.C. § 371 of PCT Application No. PCT/EP2017/062110, filed May 19, 2017, which claims priority of Italy Patent Application No. 102016000051626, filed May 19, 2016, which are hereby incorporated by reference in their entirety.

FIELD OF THE INVENTION

The invention concerns the use of compounds to promote hair growth and/or inhibit or delay hair loss in humans, and compositions for such use comprising such compounds as active principles.

PRIOR ART

The term sandalwood is referred to a class of woods from trees of the genus *Santalum*. The essential oil of sandalwood is usually extracted by steam distillation of wood from matured sandalwood trees, and is a well-known valued component for perfumes.

Among a number of different uses in the cosmetic field, mostly related to its valued scent, sandalwood oil is also the subject of patent publications regarding officinal and empirical preparations for a number of different uses, including a generic treatment of hair loss and dandruff, such as for example the patent publication CN1075250A describing a medicinal extract, defined in fact as Chinese medicine, comprising sandalwood mixed with flower bud of magnolia, rose flower, liquorice root, peony bark powder, kaempferia, lilac, herba asari, ginseng and root of angelica dahurica.

CN102000293 and CN103735443 describe similar Chinese medicines, the former made of a mixture of sandal wood, angelica roots, rhizoma kaempferiae seeds, talc, holy basil, natural indigo and spike nard, the latter made of a mixture of sandal wood, fleece flower root, pine needles and salvia miltiorrhiza, to be applied on hair.

For a substantially similar generic use, the Indian patent publication IN00177MU2002A describes a composition for the prevention of hair falling which comprises sandalwood oil mixed with coconut oil, eucalyptus oil, clove oil, lavender oil and rosemary oil.

For such empirical preparations, the specific role of each ingredient as mixed in the final oil is not defined in such publications, so that neither the specific function of the ingredient sandalwood oil in the mixtures, whether as fragrance or possibly other than that, is determined.

In any case, the main components of sandalwood oil are α-santalole β-santalol, which are alcohols basically showing a sesquiterpenic type chain. The structural formula of α-santalol is:

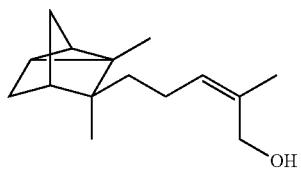 [SMILES: C/C(=C/CCC1(C)C2CC3C(C2)C31C)CO]

whereas β-santalol is:

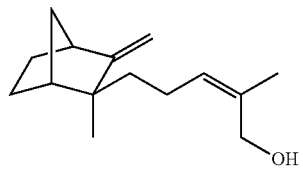 [SMILES: C=C1C2CCC(C2)C1(C)CC/C=C(/C)CO]

characterized by a terminal tricyclohept-3-yl or a bicyclohept-2-yl group, respectively.

On the other hand, the compound known as sandalore is a synthetic odorant having a fragrance similar to sandalwood and consequently used in perfumes, emollients and skin cleaning agents as a less expensive ingredient mimicking the sandalwood scent. Sandalore, as well as the structurally similar compound named brahmanol, are alcohols having a chemical structure quite distinct from the said ingredients of natural sandalwood oil, that is, α-santalol e β-santalol.

In fact sandalore, or sandal pentanol, having formula:

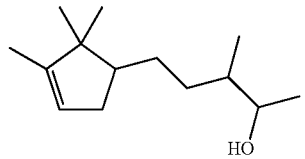

and brahmanol, or sandal cyclopentane, having formula:

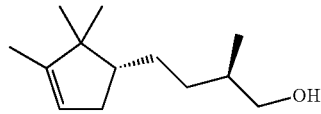

are synthetic molecules both characterized by a terminal cyclopenten-1-yl group and have no sesquiterpenic chain. They are also the subject of patent publications regarding the treatment of hair in cosmetic formulations such as shampoos and hair conditioners, however used merely as fragrances, in fact for the specific purpose of using their property of mimicking the valued sandalwood scent. For example EP1561476 describes deodorant compositions for improving deodorizing effects where, among a broad number of substances and a broad number of uses, the use of sandalore and brahmanol is also described as deodorizing fragrances in hair care products such as shampoos, conditioners, hair rinse, hair coloring agents, permanent-wave agents, wax, hair spray and mousse. The fragrance materials of natural origin to be used as fragrances in EP1561476 include sandalwood oil, and sandalore and brahmanol are defined as trade names of the above materials, thus meaning that according to this document there is no distinction between the fragrance provided by the natural extract and its synthetic substitutes.

EP1346720 relates to a deodorant composition for hair color having a similar scope. There is no description in such publications, not even generically, of such synthetic odorants for the treatment of hair loss, or for promoting hair growth.

According to Busse et al., A Synthetic Sandalwood Odorant Induces Wound-Healing Processes in Human Keratinocytes via the Olfactory Receptor OR2AT4, Journal of Investigative Dermatology, 2014, 134: 2823-2832, sandalore and brahmanol have been identified as agonists of the cutaneous olfactory receptor OR2AT4, and found to induce $Ca^{2+}$ signals in cultured human keratinocytes. The long-term stimulation of keratinocytes with sandalore positively affects cell proliferation, migration and regeneration of keratinocyte monolayers in an in vitro wound scratch assay, and sandalore stimulation enhances epidermal wound healing in human skin organ cultures.

According to Busse et al., evidence is described that natural sandalwood oil and other synthetic sandalwood odorants are not agonists of the olfactory receptor OR2AT4 and do not show the same epidermal wound healing effect.

Olfactory receptors (ORs) expression is not restricted to the nasal epithelium but it is also present in different human tissues, see Feldmesser E, Olender T, Khen M, Yanai I, Ophir R, Lancet D., Widespread ectopic expression of olfactory receptor genes. BMC Genomics. 2006 May 22; 7:121; Zhang X, Firestein S., Nose thyself: individuality in the human olfactory genome. Genome Biol. 2007; 8(11): 230; Flegel C, Manteniotis S, Osthold S, Hatt H, Gisselmann G., Expression profile of ectopic olfactory receptors determined by deep sequencing. PLoS One. 2013; 8(2):55368). Numerous studies have described physiological roles for ORs in various human cell types (Kang N, Koo J. Olfactory receptors in non-chemosensory tissues. BMB Rep. 2012 November; 45(11):612-22) such as spermatozoa (Spehr M, Gisselmann G, Poplawski A, Riffell J A, Wetzel C H, Zimmer R K, Hatt H. Identification of a testicular odorant receptor mediating human sperm chemotaxis. Science. 2003 Mar. 28; 299(5615):2054-8; Veitinger T, Riffell J R et al, Chemosensory Ca2+ dynamics correlate with diverse behavioural phenotypes in human sperm. J Biol Chem. 2011 May 13; 286(19):17311-25), prostate epithelial cells (Neuhaus E M, Zhang W, Gelis L, Deng Y, Noldus J, Hatt H. Activation of an Olfactory Receptor Inhibits Proliferation of Prostate Cancer Cells. J Biol Chem. 2009; 284(24):16218-16225), and enterochromaffin cells of the gut (Braun T, Voland P, Kunz L, Prinz C, Gratzl M. Enterochromaffin cells of the human gut: sensors for spices and odorants. Gastroenterology. 2007 May; 132(5):1890-901).

SUMMARY OF THE INVENTION

According to the present invention, it has been surprisingly found that hair growth can be promoted, and that hair loss can be inhibited or delayed, in the human scalp by the use of compounds of general formula (I):

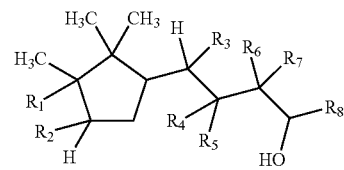

wherein:

$R_1$ and $R_2$ form together a double bond, or $R_1$ and $R_2$ form together a cyclopropyl group;

$R_3$, $R_4$ are the same or different and independently chosen from hydrogen, methyl, or $R_3$ and $R_4$ form together a double bond;

$R_5$, $R_6$ are the same or different and independently chosen from hydrogen, methyl; or $R_5$ and $R_6$ form together a double bond, or $R_5$ and $R_6$ form together a cyclopropyl group;

$R_7$=methyl, or ethyl;

$R_8$=hydrogen, or methyl.

Within the scope of the new use according to the present invention, preferred compounds of formula (I), including the aforementioned sandal pentanol (compound 1) and sandal cyclopentane (compound 5), are reported in the following table:

| Compound | | IUPAC Name | CAS No | Structural formula | Formula/MW |
|---|---|---|---|---|---|
| 1 | sandal pentanol | 3-methyl-5-(2,2,3-trimethylcyclopent-3-en-1-yl)pentan-2-ol | 65113-99-7 | | $C_{14}H_{26}O$ 210.36 |
| 2 | sandal pentenol | (4Z)-3-methyl-5-(2,2,3-trimethylcyclopent-3-en-1-yl)pent-4-en-2-ol | 67801-20-1 | | $C_{14}H_{24}O$ 208.35 |
| 3 | sandal cyclopropane | 1-methyl-2-((1,2.2-trimethylbicyclo(3.1.0)hex-3-yl)methyl)-cyclopropane-methanol | 198404-98-7 | | $C_{15}H_{26}O$ 222.37 |
| 4 | Santol pentenol | (E)-3,3-dimethyl-5-(2,2,3-trimethylcyclopent-3-en-1-yl)pent-4-en-2-ol | 107898-54-4 | | $C_{15}H_{26}O$ 222.37 |

-continued

| Compound | | IUPAC Name | CAS No | Structural formula | Formula/MW |
|---|---|---|---|---|---|
| 5 | sandal cyclopentane | 2-Methyl-4-(2,2,3-trimethyl-3-cyclopenten-1-yl)butanol | 72089-08-8 | | $C_{13}H_{24}O$ 196.34 |
| 6 | sandalrome | (E)-2-ethyl-4-(2,2,3-trimethylcyclopent-3-en-1-yl)but-2-en-1-ol | 28219-61-6 | | $C_{14}H_{24}O$ 208.35 |
| 7 | sandal butenol | (E)-2-methyl-4-(2,2,3-trimethyl-3-cyclopenten-1-yl)-2-buten-1-ol | 28219-60-5 | | $C_{13}H_{22}O$ 194.32 |

An object of the invention are also compositions for use in promoting hair growth, and/or inhibiting or delaying hair loss, suitable for topical administration on the human scalp, in which one or more compounds of formula (I) are used as active principles, preferably in a quantity between 0.1 and 10% by weight (w/w %), formulated with ingredients suitable for a topical administration.

The compositions of the invention are suitable both for a cosmetic and a therapeutic use in promoting hair growth and/or the treatment of hair loss in the human scalp, wherein at least one compound of general formula (I) is comprised as active principle.

DETAILED DESCRIPTION OF THE INVENTION

In order to best understand the characteristics and advantages of the invention, nonlimiting practical examples thereof are described below. The components are named according to the INCI nomenclature.

EXAMPLES

Example 1

Lotion

| component (INCI name) | quantity (w/w %) |
|---|---|
| Alcohol denat. | 15-35 |
| PEG-40 Hydrogenated castor oil | 0.5-3 |
| Sandal pentanol | 0.1-10.0 |
| Ethoxydiglycol | 0.25-1.0 |
| Aqua q.s. to 100 g | |

Example 2

Pre-Shampoo Mask

| component (INCI name) | quantity (w/w %) |
|---|---|
| glycerin | 1.5-4.5 |
| ammonium acryloyldimethyltaurate/vp copolymer | 1.0-2.0 |
| sandal pentanol | 0.1-10.0 |
| cyclopentasiloxane | 1.0-2.0 |
| phenoxyethanol | 0.25-0.75 |
| parfum | 0.5-1.0 |
| caprylyl glycol | 0.25-0.75 |
| phenyl trimethicone | 0.25-0.75 |
| silicone quaternium-17 | 0.1-0.4 |
| dimethicone | 0.1-0.4 |
| laureth-4 | 0.1-0.4 |
| sericin | 0.1-0.4 |
| tocopheryl acetate | 0.1-0.3 |
| laureth-23 | 0.1-0.3 |
| potassium sorbate | 0.05-0.15 |
| ammonium glycyrrhizate | 0.05-0.15 |
| citric acid | 0.04-0.08 |
| disodium edta | 0.025-0.075 |
| ethylhexyl methoxycinnamate | 0.025-0.075 |
| dimethiconol | 0.025-0.075 |
| aqua q.s. to 100 g | |

Example 3

Strengthening Styling Gel

| Component (INCI name) | quantity (w/w %) |
|---|---|
| sandal pentanol | 0.1-10.0 |
| PEG-40 hydrogenated castor oil | 1-3 |
| parfum | 0.5-1.5 |
| polyacrylate-14 | 0.5-1.5 |
| hydroxypropyl guar | 0.5-1.5 |
| hydrogenated starch hydrolysate | 0.5-1.5 |
| sodium hydroxymethylglycinate | 0.25-1.0 |
| benzophenone-4 | 0.15-0.45 |
| disodium edta | 0.05-0.15 |
| polyquaternium-11 | 0.0025-0.025 |
| aqua q.s. to 100 g | |

Example 4

Fortifying Hair Conditioner

| Component (INCI name) | quantity (w/w %) |
|---|---|
| cetearyl alcohol | 15-25 |
| glyceryl stearate | 15-25 |
| dimethicone | 10-20 |
| C12-13 alkyl lactate | 5-15 |
| cetrimonium chloride | 2.5-7.5 |
| PEG-100 stearate | 2.5-7.5 |
| cyclopentasiloxane | 2-6 |
| xylitol | 2-6 |
| sandal pentanol | 0.1-10.0 |
| hydroxyethylcellulose | 1-3 |
| dimethiconol | 1-3 |
| benzyl alcohol | 0.1-1.0 |
| panthenol | 1-3 |
| parfum | 1-2 |
| bis-isobutyl PEG/PPG-20/35/ amodimethicone copolymer | 0.5-1.0 |
| phytantriol | 0.5-1.0 |
| sodium benzoate | 0.5-1.0 |
| sodium dehydroacetate | 0.5-1.0 |
| cetyl ethylhexanoate | 0.5-1.0 |
| butylene glycol | 0.5-1.0 |
| disodium edta | 0.2-0.6 |
| polysorbate 80 | 0.2-0.6 |
| sericin | 0.2-0.6 |
| dehydroacetic acid | 0.1-0.3 |
| yeast polysaccharides | 0.1-0.3 |
| gluconolactone | 0.05-0.15 |
| aqua q.s. to 100 g | |

Example 5

Revitalizing Shampoo

| Component (INCI name) | quantity (w/w %) |
|---|---|
| magnesium laureth sulfate | 5-10 |
| sodium lauroyl sarcosinate | 2-3 |
| sandal pentanol | 0.1-10.0 |
| disodium laureth sulfosuccinate | 1.5-2.5 |
| PEG-200 hydrogenated glyceryl palmate | 1-2 |
| cocamide mipa | 0.5-1.5 |
| parfum | 0.5-1 |
| glycol distearate | 0.5-1 |
| PEG-7 glyceryl cocoate | 0.25-0.75 |
| betaine | 0.25-0.75 |
| lauryl methyl gluceth-10 hydroxypropyldimonium chloride | 0.25-0.75 |
| laureth-7 | 0.25-0.75 |
| polyquaternium-10 | 0.25-0.75 |
| sodium hydroxymethylglycinate | 0.25-0.75 |
| potassium undecylenoyl hydrolyzed wheat protein | 0.2-0.4 |
| panthenol | 0.1-0.3 |
| tetrasodium edta | 0.1-0.3 |
| phenyl trimethicone | 0.05-0.15 |
| silicone quaternium-17 | 0.05-0.12 |
| laureth-4 | 0.05-0.12 |
| laureth-23 | 0.025-0.075 |
| sodium cocoamphoacetate | 0.025-0.075 |
| BHA | 1 0.005-0.015 |
| aqua q.s. to 100 g | |

Example 6

Mousse

| Component (INCI name) | quantity (w/w %) |
|---|---|
| alcohol | 10-20 |
| sandal pentanol | 0.1-10.0 |
| PEG-40 hydrogenated castor oil | 1-2 |
| glycerin | 1-1.5 |
| sodium olivamphoacetate | 0.5-1.5 |
| parfum | 0.5-1 |
| tocopherol | 0.05-0.15 |
| disodium EDTA | 0.025-0.075 |
| polyquaternium-16 | 0.025-0.075 |
| potassium metabisulfite | 0.01-0.03 |
| aqua q.s. to 100 q | |

BRIEF DESCRIPTION OF THE DRAWINGS

FIG. 1 shows immunofluorescence images taken from samples of human scalp skin tissues and hair follicles (HFs).

FIG. 2 shows a diagram relating to hair shaft elongation.

FIG. 3 shows a diagram relating to hair growth cycle, with particular reference to the catagen phase.

FIG. 4 shows a diagram relating to hair matrix keratinocyte proliferation and apoptosis.

FIG. 5 shows a diagram relating to the catagen-promoting growth factor TGFβ2.

FIGS. 1 to 5 concern the results obtained in the following experimental study, and are thus described in detail in the following description.

Experimental Study

Figure 1:
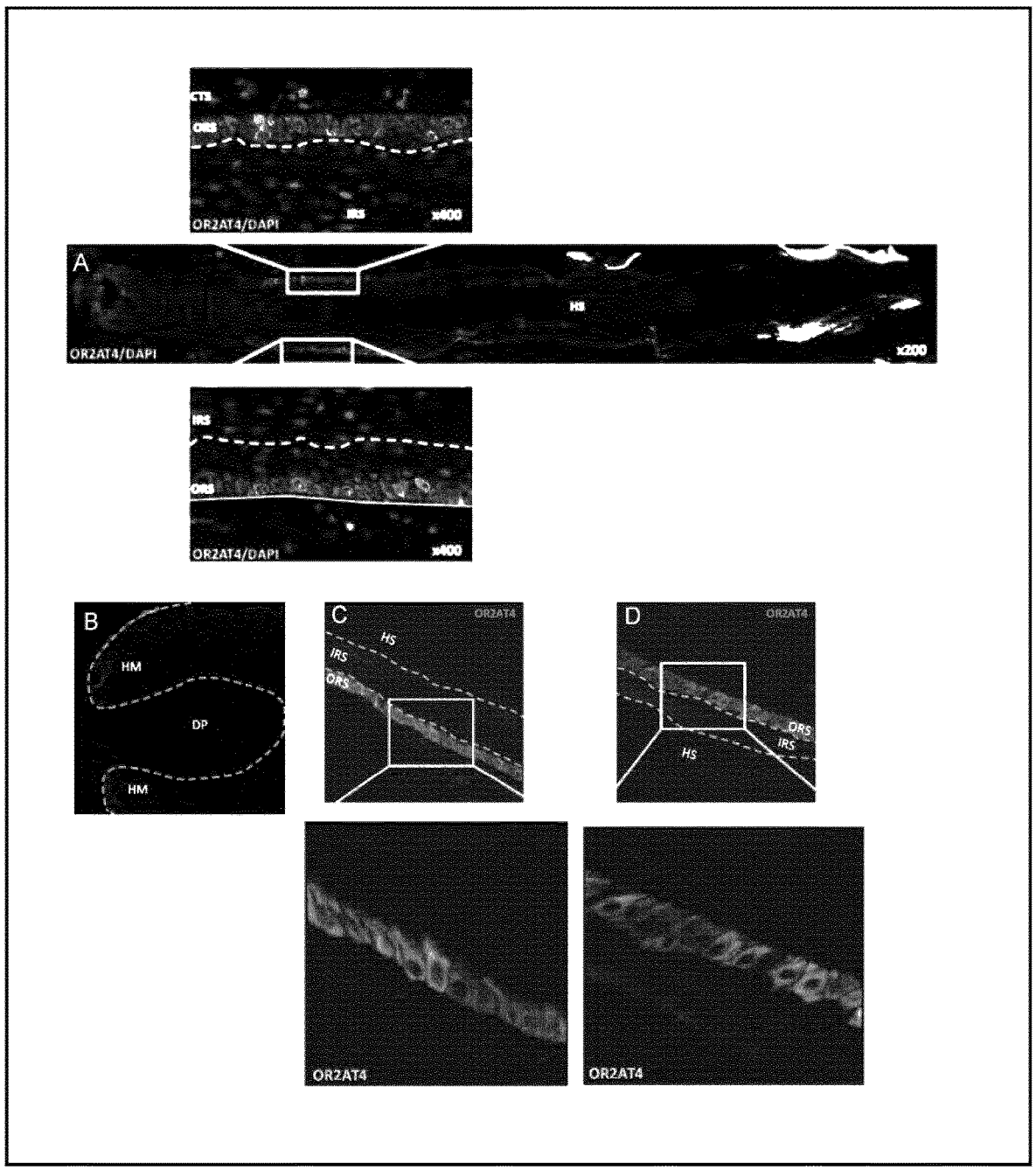
With reference to FIGS. 1 to 5 of the accompanying drawings.

The said compound 1 according to the invention, i.e. sandal pentanol, was chosen among the compounds of formula (I) to be tested for experimental purposes as follows. Sandal pentanol is named Sandalore in the diagrams of FIGS. 2-5.

Study Design

As a first step, standard immunofluorescence technique was used on human scalp skin tissue sections from healthy donors in order to assess whether OR2AT4 is expressed in human scalp hair follicles (HFs).

Then, in order to assess whether stimulation of OR2AT4 can influence human hair growth, microdissected HFs were treated with sandal pentanol at a concentration of 500 μM, as the agonist and a hair shaft elongation measurement was performed (see Philpott et al., 1990). In addition, a kinase assay was conducted in order to identify which signalling pathways are involved in the specific stimulation of OR2AT4 by sandal pentanol.

Subsequently, in order to confirm that the anagen prolonging effect of sandal pentanol is specific, a HF organ culture was performed using sandal pentanol as the agonist and a specific antagonist, Phenirat (phenoxyethyl isobutyrate), a synthetic fragrance, see the Busse et al. reference mentioned above.

HFs were treated with either the vehicle, sandal pentanol, Phenirat or a mixture of sandal pentanol and Phenirat. To analyse modifications of the hair cycle, Ki67/TUNEL were performed and used to evaluate hair cycle score and hair matrix keratinocytes proliferation and apoptosis.

In addition, TGFβ2, a potent catagen inducer, was investigated with reference to the same above compounds.

In order to downregulate the expression of OR2AT4 in human HFs and to study the effect of this in hair growth, HFs were transfected with OR2AT4-siRNA.

qRT-PCR and (immuno-)histomorphometry analyses were employed to confirm a successfully siRNA-mediated downregulation of OR2AT4 gene and protein in microdissected HFs. Finally, in order to investigate how the knockdown of OR2AT4 influences human hair growth, Ki67/TUNEL immunofluorescence was used to quantify the hair cycle score and hair matrix keratinocytes proliferation and apoptosis.

To check whether the knockdown can influence the catagen induction, TGF62 expression was analysed by immunofluorescence.

Materials and Methods

Tissue Specimens

Temporal and occipital normal human scalp skin was obtained from healthy donors (in an age range 38-69 years) undergoing routine face-lift surgery after informed consent and ethical approval.

Immunofluorescence

OCT embedded samples were sectioned (6 μm thickness) with a cryostat. Sections were fixed in 4% paraformaldehyde, pre-incubated with 10% of goat serum (for OR2AT4) or 5% goat serum+0.3% Tritton X-100 (for cleaved-caspase 3) and incubated with the corresponding primary antibody at 4° C. overnight (1/100 for OR2AT4 and 1/400 for cleaved-caspase 3). Secondary antibody incubation was performed at RT for 45 min. Counterstaining with DAPI (1 μg/mL) was performed to visualize nuclei. For TGFb2, samples were fixed in acetone and the endogenous peroxidases were blocked with 3% of $H_2O_2$. This step was followed by an avidin-biotin blocking step and a preincubation with TNB buffer (Tris HCl+NaCl+Casein). The corresponding primary antibody was incubated at 4° C. overnight (1/1000 for TGFb2). Secondary antibody incubation was performed at RT for 45 min before using the Tyramide signal amplification kit (Perkin Elmer). Counterstaining with DAPI was performed to visualize nuclei. To stain apoptotic and proliferating cells, we have used the apoptag kit (Merck Milipore) following manufacture's protocol followed by Ki67 staining. The primary antibody was incubated overnight (Ki67, 1/20) after the TdT-enzyme step. The secondary antibody was incubated for 45 min at RT after the fluorescent-labelled anti-Digoxigenin step of the apoptag kit. Counterstaining with DAPI was performed to visualize nuclei. Negative controls were performed by omitting the primary antibody. Images were taken using a Keyence fluorescence microscope (Osaka, Japan) maintaining a constant set exposure time throughout imaging for further analysis.

HF Organ Culture

Human scalp samples were obtained after face-lifting procedure and used at the same day for microdissecting human anagen VI scalp HFs. Microdissected human scalp HFs were cultured at 37° C. with 5% $CO_2$ in a minimal media of William's E media (Gibco, Life technologies) supplemented with 2 mM of L-glutamine (Gibco), 10 ng/ml hydrocortisone (Sigma-Aldrich), 10 μg/ml insulin (Sigma-Aldrich) and 1% penicillin/streptomycin mix (Gibco) (WEM) as previously described (Philpott, 1990; Kloepper, 2010; Langan et al, 2015).

1) Chemical Stimulation of Human Microdissected HFs with OR2AT4 Sandal Pentanol (Agonist) and Phenirat (Antagonist)

After 24 h of incubation, WEM medium was replaced and HFs were treated with the corresponding substances for 6 days following experimental conditions. HFs were treated either with vehicle (0.1% DMSO), sandal pentanol (500 μM), Phenirat (in a ratio 1:1 to the agonist), or a mixture sandal pentanol+Phenirat.

Phenirat was added 30 min before sandal pentanol. Hair shaft elongation was measured daily using an inverted binocular microscope (Philpott et al., 1990) and culture medium was replaced every second day. HFs were then embedded in cryomatrix (Fisher Scientific) and snap frozen in liquid nitrogen. Sections of 6 μm thickness were cut with a cryostat and stored at −80° C. for further immunohistochemical analysis.

Quantitative (Immuno-)Histomorphometry

Staining intensity was evaluated in well-defined reference areas by quantitative (immuno-)histomorphometry, as previously described (Bertolini et al., 2014) using NIH IMAGE software (NIH, Bethesda, Md., USA).

Statistical Analyses

All data are expressed as mean±SEM and were analysed by One Way Anova or Kruskall Wallis test when more than 2 groups were compared and Student's t-test or Mann-Whitney test when sandal pentanol treatment was compared to vehicle (Graph Pad Prism 6, GraphPad Software, San Diego, Calif., USA).

Results

Results are described with reference to the enclosed drawings of FIGS. 1 to 5.

1) Human HFs Express the Olfactory Receptor 2AT4

Firstly the presence of the olfactory receptor 2AT4 (OR2AT4) in HFs was investigated. OR2AT4 was observed in the suprabulbar outer root sheath (ORS) keratinocytes of human scalp anagen HFs, as shown by immunofluorescence in FIG. 1.

Pictures A) to D) from FIG. 1 represent OR2AT4 immunofluorescence in HFs in human scalp skin (see picture A and corresponding enlargements) and microdissected HFs (see pictures B-D and corresponding enlargements) from three different donors (n=3). CTS stands for connective tissue sheath, DP for dermal papilla, HM for hair matrix, IRS for inner root sheath, ORS for outer root sheath, HS for hair shaft, HB for hair bulb, HF for hair follicles. Dotted lines delineate the IRS (inner root sheath), ORS (outer root sheath) and DP (dermal papilla).

FIG. 1 shows that OR2AT4 is expressed in suprabulbar ORS keratinocytes of anagen scalp HFs and in suprabulbar and bulbar ORS, and in hair matrix tips keratinocytes in microdissected anagen HFs.

Microdissected anagen HFs (Philpott model) revealed OR2AT4 cells in the hair bulb, namely in ORS and hair matrix (HM) tips, see FIG. 1B, in addition to the characteristic suprabulbar intrafollicular expression, see FIG. 1D.

2) Specific Stimulation of OR2AT4 by Sandal Pentanol Promotes Hair Shaft Elongation and Inhibits Apoptotic Signalling Pathway To check whether the activation of OR2AT4 can influence the hair cycle of human HF, microdissected human HFs were specifically stimulated with the potential agonist, sandal pentanol. The effect of the sandal pentanol treatment was evaluated by measuring hair shaft elongation compared to vehicle.

Figure 2:
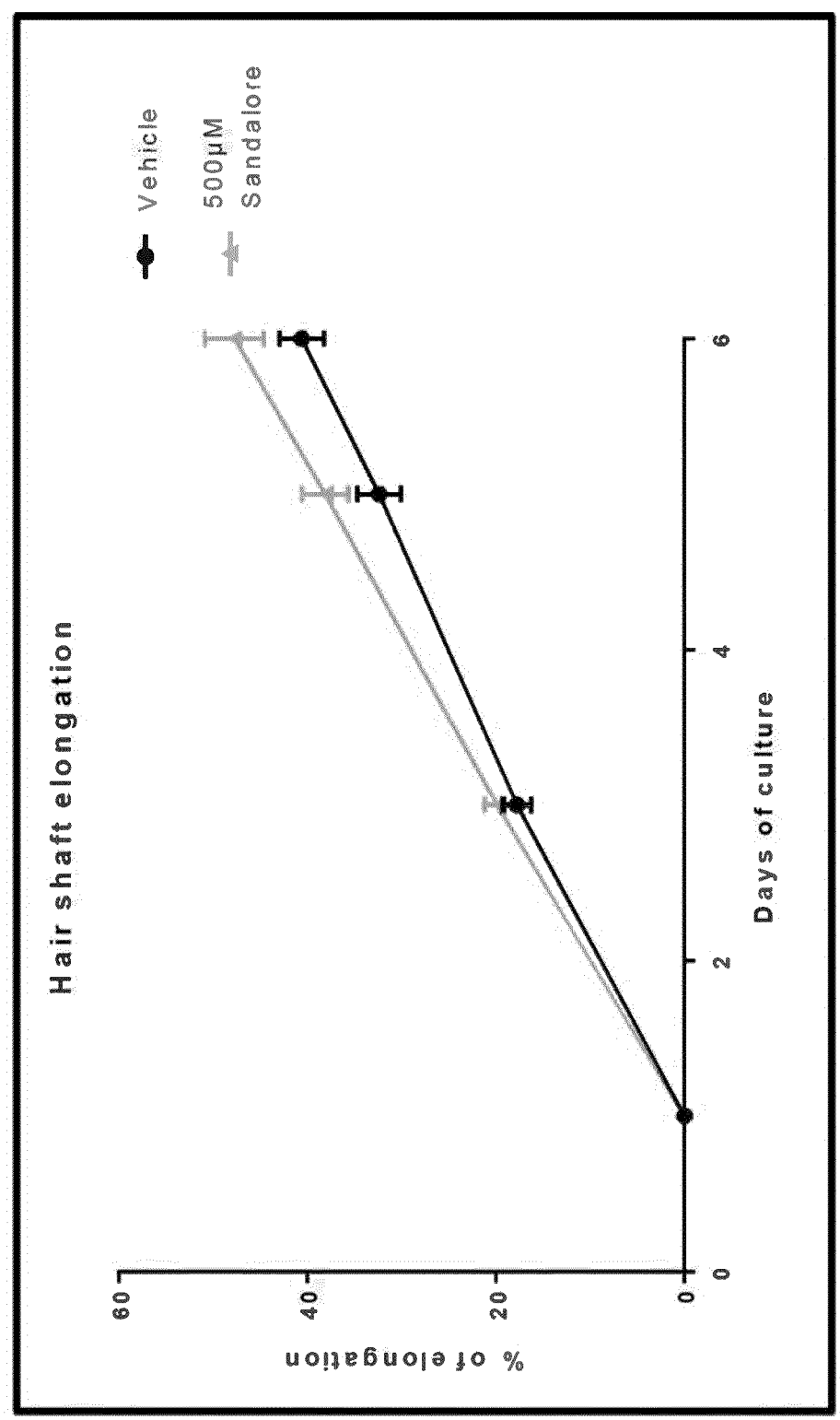

HF elongation was measured in cultured microdissected HFs. Mean±SEM, n=18 HFs for each donor, 2 donors, Student's t-test, Graph Pad Prism 6. Despite interindividual differences, the results reveal that sandal pentanol at concentration 500 μM stimulates hair shaft elongation of cultured microdissected HFs deriving from two donors, as shown in the diagram of FIG. 2 reporting % elongation versus days of culture, sandalore compared to vehicle.

3) The Activation of OR2AT4 by Sandal Pentanol Significantly Delays Catagen Induction and Decreases Apoptosis in Human Hair Matrix Keratinocytes To investigate the specificity of the effect on hair growth of OR2AT4 stimulation by sandal pentanol, microdissected HFs were cultured with sandal pentanol and/or Phenirat, and hair cycle performed staging analysis as previously described (Kloepper, 2010; Langan et al, 2015). Hair cycle score was measured both in treated and vehicle HFs after 6 days of culture. N=16-24 HFs from 3 patients, Mean±SEM, Kruskal Wallis test and Dunn's multiple comparisons test as post hoc test, ns, Mann-Whitney test, #p<0.05, Graph Pad Prism 6.

Figure 3:
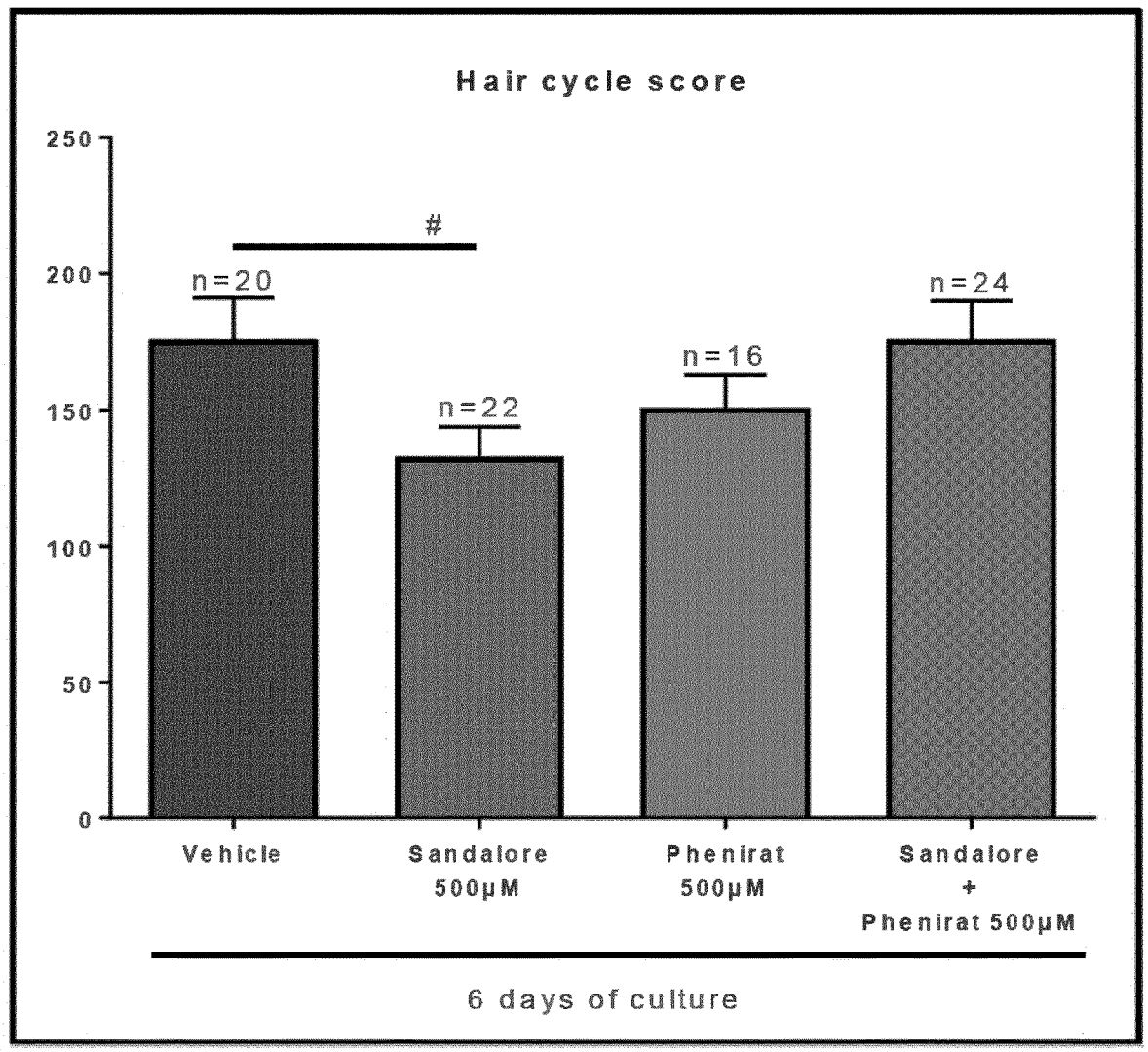

The obtained results indicate that the specific stimulation of OR2AT4 by sandal pentanol alone at concentration 500 μM delayed catagen induction in treated HFs compared to vehicle after 6 days of culture, as shown in the diagram of FIG. 3. On the contrary, both comparative reference Phenirat alone and the mixture of sandal pentanol administered together with Phenirat did not prolong anagen in treated HFs compared to vehicle. The data suggest that the stimulation of OR2AT4 by sandal pentanol promotes catagen delay, whilst these effects are counteracted by OR2AT4 inhibition when using Phenirat.

To sum up, FIG. 3 shows that the compound of the invention significantly delays catagen development.

4) Sandal Pentanol Significantly Decreases Hair Matrix Keratinocytes Apoptosis

Figure 4:
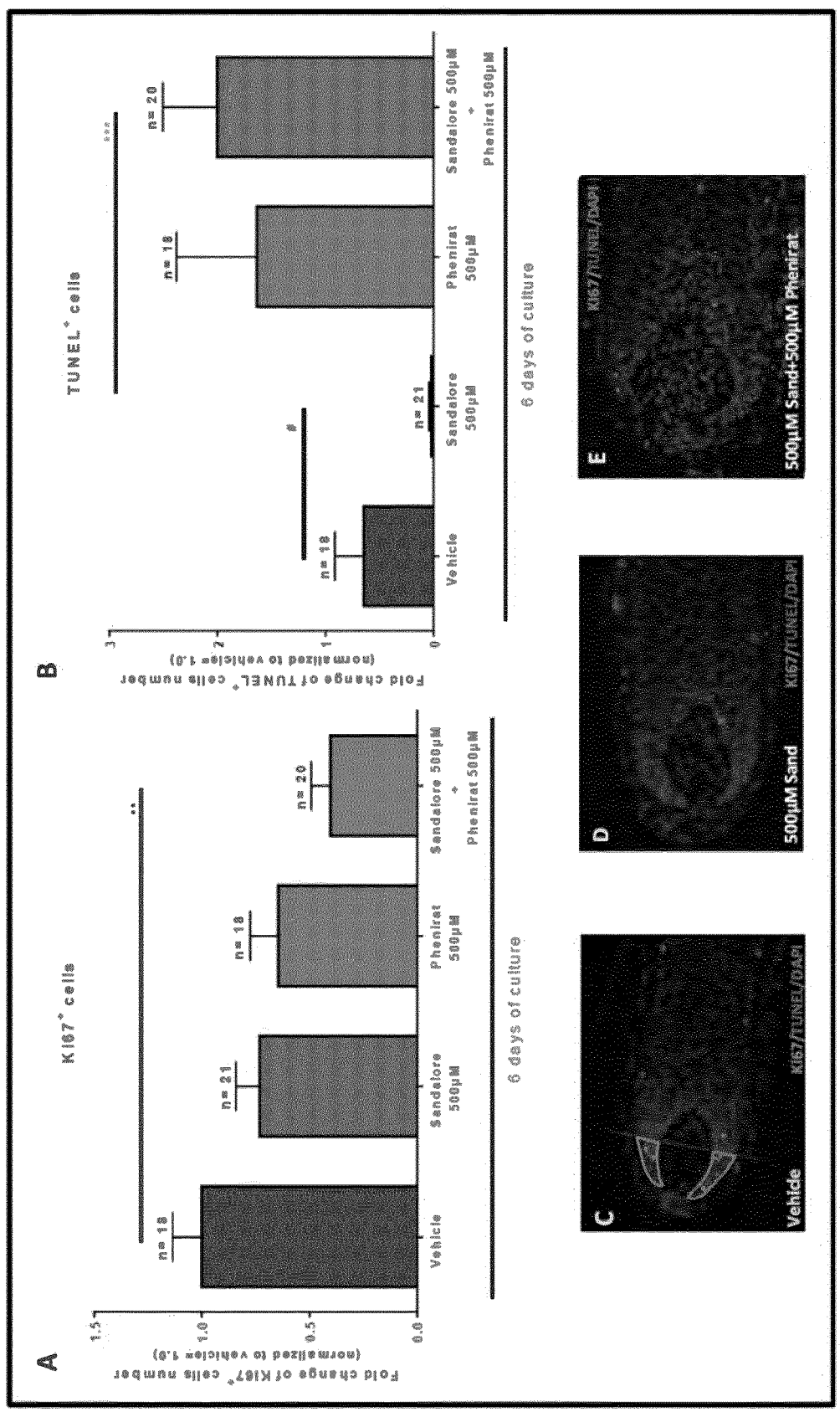

With reference to the evidence of FIG. 4, to investigate whether sandal pentanol influences hair matrix keratinocytes proliferation and apoptosis, Ki67/TUNEL staining was performed. Proliferating (diagram of FIG. 4A) and apoptotic (diagram of FIG. 4B) hair matrix keratinocytes were counted in the hair matrix of treated and vehicle HFs. Representative pictures of Ki67/TUNEL are shown in FIG. 4 from C to E. Mean±SEM, n=18-21 HFs from 3 patients, Kruskal-Wallis test and Dunn's multiple comparisons test as post hoc test, p<0.01, *p<0.001, Mann-Whitney test #p<0.05, Graph Pad Prism 6.

After 6 day-culture, hair matrix keratinocyte proliferation did not change in HFs treated with sandal pentanol or Phenirat alone. However co-administration of the specific antagonist of OR2AT4, Phenirat, together with sandal pentanol induced a significant decrease on the hair matrix keratinocyte proliferation as shown in FIG. 4A.

Sandal pentanol treatment significantly decreased hair matrix keratinocyte apoptosis, whilst co-administration of sandal pentanol+Phenirat significantly increased hair matrix keratinocyte apoptosis, as shown in FIG. 4B.

5) Specific Stimulation of OR2AT4 by Sandal Pentanol Significantly Decreased the Catagen-Promoting Growth Factor TOFβ2

Figure 5:
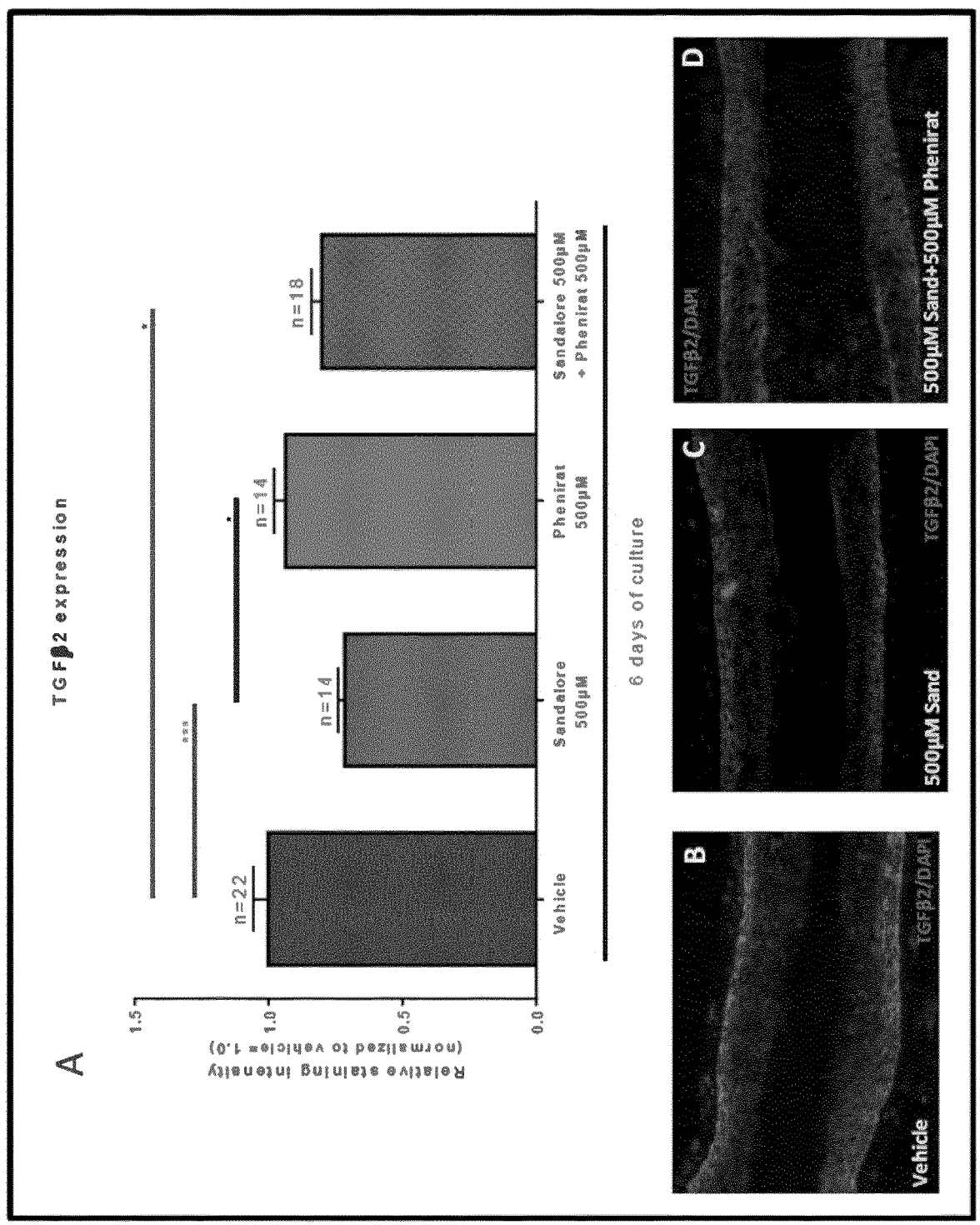

With reference to the evidence of FIG. 5, to further investigate how OR agonist and antagonist affect HFs growth, the expression of the relevant catagen-promoting growth factor during physiological human HF cycling, i.e. TGFβ2 (Soma et al., 2002), in the proximal ORs was examined. After 6 day-treatment with sandal pentanol, a significant decrease in TGFβ2 expression at the protein level was observed, while no change was detected by blocking the receptor with Phenirat. In this case the co-administration of sandal pentanol with Phenirat showed a comparable result as obtained by administration of sandal pentanol alone, as shown in the diagram of FIG. 5A. TGFβ2 expression was measured in ORS keratinocytes in treated and vehicle HFs.

Corresponding representative pictures of TGFβ32 immunofluorescence are shown in FIG. 5, B (vehicle), C (sandalore), D (sandalore+Phenirat).

TGFβ2 expression was quantified using Image J. Mean±SEM, n=14-22 HFs from 2 patients, Kruskal-Wallis and Dunn's multiple comparisons test as post hoc test, *p<0.05, ***p<0.001, and Mann-Whitney test, ns. Graph Pad Prism 6.

CONCLUSIONS

The above results overall show that OR2AT4 is a hair growth modulator and the compound of the invention is an anagen-prolonging agent. Stimulation of OR2AT4 by the compound of the invention increases hair shaft elongation and delays catagen phase transition, while the effect is not obtained with the OR2AT4 inhibitor Phenirat, and is substantially counteracted when the compound of the invention is co-administered with Phenirat.

Stimulation of OR2AT4 by the compound of the invention modulates apoptotic signalling pathways and significantly decreases apoptosis in human hair matrix keratinocytes, while this effect is not obtained with Phenirat and is substantially counteracted when the compound of the invention is co-administered with Phenirat. Stimulation of OR2AT4 by the compound of the invention significantly decreases the relevant catagen-promoting growth factor, TGFβ2, while this effect is not obtained with Phenirat.

In general terms, the experimental evidence shows that the compounds of formula (I) as defined above can be effectively used for promoting hair growth and/or inhibiting or delaying hair loss in human scalp.

The invention claimed is:

1. A method of promoting hair growth and/or inhibiting or delaying hair loss in the scalp of a human subject, said method comprising:

administering, to the subject in need thereof, 3-methyl-5-(2,2,3-trimethylcyclopent-3-en-1-yl)pentan-2-ol.

2. The method according to claim 1, wherein a cosmetic composition comprising said 3-methyl-5-(2,2,3-trimethylcyclopent-3-en-1-yl)pentan-2-ol is administered to said subject.

3. The method according to claim 2, wherein the cosmetic composition comprises at least 3-methyl-5-(2,2,3-trimethylcyclopent-3-en-1-yl)pentan-2-ol as an active principle in a quantity between 0.1 and 10% by weight (w/w %), and is formulated with ingredients suitable for topical administration.

4. The method according to claim 1, wherein said 3-methyl-5-(2,2,3-trimethylcyclopent-3-en-1-yl)pentan-2-ol is administered topically.

\* \* \* \* \*